United States Patent [19]

Barone

[11] 3,987,069

[45] Oct. 19, 1976

[54] PREPARATION OF OXIRANE COMPOUNDS BY AUTOXIDATION

[75] Inventor: Bruno J. Barone, Houston, Tex.

[73] Assignee: Petro-Tex Chemical Corporation, Houston, Tex.

[22] Filed: Aug. 9, 1971

[21] Appl. No.: 170,283

[52] U.S. Cl. ........................................ 260/348.5 V
[51] Int. Cl.² ................................... C07D 301/22
[58] Field of Search ........................... 260/348.5 V

[56] References Cited
FOREIGN PATENTS OR APPLICATIONS

| | | |
|---|---|---|
| 1,088,810 | 10/1967 | United Kingdom |
| 1,138,361 | 1/1969 | United Kingdom |
| 1,026,971 | 4/1966 | United Kingdom |

OTHER PUBLICATIONS

Chemical Abstracts, vol. 72, (1970), 21397m.
Chemical Abstracts, vol. 74, (1971), 88364h.

*Primary Examiner*—Norma S. Milestone
*Attorney, Agent, or Firm*—N. Elton Dry; Kenneth H. Johnson

[57] ABSTRACT

Boron and lithium phosphate have been found to provide high selectivity to epoxides in the autoxidation of olefinic compounds when said phosphates are employed in catalytic amounts. Selectivities for the epoxide as high as 65.8% have been achieved at conversions of about 14 mole %.

7 Claims, No Drawings

PREPARATION OF OXIRANE COMPOUNDS BY AUTOXIDATION

BACKGROUND OF THE INVENTION

The present invention relates to the preparation of olefin oxides and in particular relates to new catalysts for use in the process of autoxidation of ethylenically unsaturated organic compounds to the corresponding oxirane compounds.

A number of catalysts have been employed in the liquid phase oxidation of ethylenically unsaturated organic compounds. U.S. Pat. No. 3,259,638 shows the use of compounds of Groups IV-A, V-A or VI-A of the Periodic Table excluding chromium. Selectivity for the epoxide with each catalyst was less than 50%. The major by-products were epoxy-alcohols. The general disadvantages of the prior methods, particularly the catalysts employed in such autoxidations were long reaction times, low conversions and low selectivity to the epoxide, i.e., usually less than 50%. The term autoxidation is understood to mean the reaction of a substance with molecular oxygen without the intervention of a flame. In addition to the epoxide a number of by-products are possible from the autoxidation of olefins, e.g., epoxy-alcohols, diols, olefin hydroperoxides, aldehydes, ketones, water and carbon dioxide. If the desired product is the epoxide then the production of such by-products and the necessity of separating them from the epoxide can make the process economically unattractive. The by-products are often quite useful, e.g., acetone is a common product and the uses of acetone are well known, however, acetone is a far less valuable material than many of the common or desirable olefinic starting materials.

It is an object of this invention to provide an improved process for the autoxidation of ethylenically unsaturated organic compounds. It is a further object of this invention to provide a process which has high selectivity for epoxides. These and other objects will become apparent from the discussion below.

DESCRIPTION OF THE INVENTION

It has been found that ethylenically unsaturated organic compounds can be autoxidized to oxirane compounds by a process comprising contacting an ethylenically unsaturated organic compound with molecular oxygen in liquid phase in the presence of a catalytic amount of lithium phosphate or boron phosphate. The amount of phosphate is generally about 0.05 to about 0.8 weight percent based on the olefinic starting material, more preferably an amount in the range of 0.1 to 0.4 weight percent of phosphate on the same basis. The total amount of phosphate can be added to the reaction initially or it can be added incrementally throughout the reaction. The presence of other known catalysts, such as vanadium naphthenate, tungstic acid, niobium pentoxide, vanadium pentoxide, molybdenum hexacarbonyl, cobalt naphthenate, chromium naphthenate and the like, which are used for the preparation of epoxides has not been found to be detrimental, however, no advantage has been observed in this regard.

The present reaction is an autoxidation carried out at somewhat elevated temperatures. Generally the temperatures which are most suitable for the oxidation will be between about 70°–140° C. and more preferably about 80°–110° C. In autoxidations there is usually an induction period during which the reaction proceeds very slowly. During this period the production of epoxide is slow, however, the induction period can be reduced by the use of high initial temperatures, i.e., 130°–140° C. However, once the reaction is initiated the temperature is reduced, e.g., 70°–120° C. Temperatures higher than 120° C should not be employed after the reaction has been initiated since the possibility of further oxidation is enhanced.

The induction period mentioned above can also be reduced by the addition of an initiator such as some of the hydroperoxide by-product which may be produced. Other initiators are free radical initiators such as $\alpha$-methyl benzyl hydroperoxide, $\alpha$-methyl-p-methyl-benzenyl hydroperoxide, $\alpha$-methyl-$\alpha'$-n-propyl-p-xylene dihydroperoxide, ethyl acetoacetate, phenylacetone, acetylacetone and the like.

The autoxidation is carried out by contacting an olefinically unsaturated compound in liquid phase at the temperatures and conditions set out herein with molecular oxygen. The oxygen can be furnished as pure oxygen with inert gases, such as helium or nitrogen in the same or substantially different proportions as oxygen is found in air.

Sufficient pressure is employed so as to maintain the reaction mixture in liquid phase. This will usually require more than atmospheric pressure, although some of the hydrocarbons encompassed herein are liquid at atmospheric pressure at temperatures up to the 120° C. maximum. Generally, however, pressure will be required. It is not necessary to use any more pressure than is necessary to maintain the liquid phase since oxygen is not believed to be the rate determining factor in the reaction. Pressures of atmospheric up to about 1000 psi will usually be sufficient.

The reaction is performed under liquid phase conditions and, preferably, the ethylenically unsaturated compound is employed in excess and conveniently serves as the reaction solvent. If desired, however, other solvents which are inert to the oxidation conditions can be employed such as the esters of aliphatic alcohols and carboxylic acids, hydrocarbons, saturated ethers and alcohols, water and mixtures thereof. In general, any organic liquid that is inert to the reactants and to the oxidation conditions can be employed for the reaction solvent in my invention. Generally it is convenient to employ organic liquids having from 1 to about 25 carbons; preferably solvents having from 1 to 6 carbons are used. Illustrative solvents of the aforementioned classes include the following esters: methyl acetate, ethyl acetate, n-propylpropionate, isopropyl acetate, ethylpropionate, n-butylbutyrate, sec-butyl acetate, isobutylacetate, ethyl-n-butyrate, n-butyl acetate, isoamyl acetate, n-amyl acetate, glycol diformate, furfural acetate, isoamyl n-butyrate, ethylacetyl acetate, diethyl oxalate, glycol diacetate, isoamyl isovalerate, n-dibutyl oxalate, etc.

Various aliphatic hydroxy compounds can be employed such as methanol, ethanol, propanol, isopropanol, butanol, isobutanol, amyl alcohol, isoamyl alcohol, hexanol, isohexanol, heptanol, isoheptanol, 3-methylhexanol-1, lauryl alcohol, 3,4-diethylheptanol-1, 4-ethylhexanol ethylene glycol, propylene glycol, etc.

Various ethers can also be employed including the ethers of the aforementioned aliphatic alcohols such as methyl ethyl ether, diethyl ether, dioxane, diisopropyl ether, diisoamyl ether, diethylene glycol diethyl ether, tetraethylene glycol dimethyl ether, ethyl heptyl ether, isobutyl amyl ether, lauryl ethyl ether, etc.

Hydrocarbons including the saturated and aromatic hydrocarbons can of course be employed as suitable inert solvents, e.g., pentane, hexane, heptane, octane, isooctane, decane, dodecane, kerosene, naphtha, benzene, xylene, toluene, cumene, isocumene, naphthalene, etc.

In addition other inert diluents such as the nitro or halo substituted hydrocarbons are suitable, e.g., nitrobenzene, trichlorobenzene, carbon tetrachloride and the like.

The ethylenically unsaturated compounds which may be epoxidized by the process of the invention include substituted and unsubstituted aliphatic and alicyclic olefins which may be, for example, hydrocarbons, esters, alcohols, ketones or ethers.

A wide variety of ethylenically unsaturated compounds can be epoxidized in accordance with the process. In general, any organic olefin, preferably a hydrocarbon havng from 2 to about 30 carbon atoms can be oxidized, preferably 3 or more carbon atoms, more preferably olefinically unsaturated compounds having from 3 to 12 carbon atoms are oxidized. The aliphatic hydrocarbon mono-olefins include: ethylene, propylene, butene-1, butene-2, isobutene, pentene-1, pentene-2, hexene, isohexene, heptene, 3-methylhexene-1, octene-1, isooctene, nonene, decene, dodecene, tridecene, pentadecene, octadecene, eicosene, docosene, tricosene, tetracosene, pentacosene, styrene, methyl styrene, vinyl toluene, etc. Examples of hydrocarbon diolefins which can also be oxidized include: pentadiene, hexadiene, octadiene, decadiene, tridecadiene, eicosadiene, tetracosadiene, etc. The alicyclic olefins are illustrated by cyclopentene, cyclohexene, cycloheptene, methylcyclohexene, isopropylcyclohexene, butylcyclohexene, octaylcyclohexene, dodecylcyclohexene, vinyl cyclohexene, phenyl cyclohexene, etc.

Olefins having halogen, oxygen, sulfur and other similar substituents may be used. Such substituted olefins are, such as, methyl-methacrylate, methyl oleate, methyl vinyl ketone and allyl chloride. In general all olefinic materials within the ranges specified, which have been epoxidized by the methods of the previously used, including unsaturated polymers can be epoxidized by the process of the invention.

The epoxides produced by this invention have a great deal of utility in the preparation of epoxy resins or in other resins where coupling or crosslinking is desirable. In a particular case the epoxide produced is the precursor of a valuable diolefin, e.g., 2-methyl butene-2 is oxidized to 2,3-epoxy-2-methyl butane by the improved process of the present invention. The 2,3-epoxy-2-methylbutane is isomerized to the allylic alcohol form and dehydrated to isoprene, which is used to prepare polyisoprene a highly desirable synthetic rubber. The 2,3-epoxy-2-methylbutane can be concurrently isomerized and dehydrated in liquid phase, with or without a diluent such as isopentane or hexane, preferably without a diluent by passing a stream of 2,3-epoxy-2-methylbutane through a bed of acid catalyst at temperatures of 200° to 400° C. and 15 to 1000 p.s.i.g. The acid catalysts suitably used for simultaneous isomerization and dehydration are, such as, acidic metal, e.g., alumina, chromia, thoria and titania oxides; siliceous refractory oxides, e.g., silica-alumina, silica-magnexia, silica-titania and silica-magnesia-zirconia; and alkali and alkaline earth metal phosphates, e.g., lithium phosphate and magnesium phosphate.

In carrying out the process of the invention an olefinically unsaturated compound and oxygen are contacted in the presence of the phosphate catalyst. It has been found convenient to carry out this contacting by dispersing the catalyst in the liquid phase and passing the gas containing molecular oxygen into this mixture. The catalyst is easily separated from the other materials since it is a solid in the reaction. The process is as easily adapted to either batch or continuous process operation using conventional equipment.

The following examples will illustrate the operation of the invention and the advantages to be derived therefrom. The apparatus used in each of the following examples was a 3,000 psi magnetically stirred, 1.4 liter, stainless steel autoclave, equipped with a Dispersamax agitator, reflux condenser and internal water cooling coil. The olefinic feed, and other materials for the reaction were charged to the reactor. Oxygen containing gas was added continuously with sufficient pressure to maintain the liquid phase. Inlet gas was measured by following the pressure drop in a standardized metering vessel and fed into the autoclave through a ballast type pressure regulator. Exit gas, at atmospheric pressure was then passed through three dry ice traps, an ascarite trap, a wet test meter and then vented. Air was employed in the present examples unless otherwise indicated. In the runs using air a Beckman E-2 oxygen analyzer was inserted after the dry ice traps and the oxygen content of the off gases monitored so that the reaction was not oxygen starved. This can be avoided by adjusting the gas flow to provide a minimum oxygen content for the off gases, e.g., more than about 3 vol. %. Analysis was by gas chromatograph. Epoxide content was determined by both gas chromatography and the chlorohydrin chemical method described in Organic Analysis Interscience Publishers, N. Y. 1953, Vol. 1, page 134.

EXAMPLES

These examples demonstrate both the boron phosphate and lithium phosphate catalysts. The range of the Examples demonstrates a number of the variables for the operation of the process. The oxidation was carried out with air at 400 p.s.i., except for Example 8 and 9 which employed oxygen at 600 p.s.i. Examples 8 and 9 are controls. Example 7 compares phosphoric acid to the catalysts. Example 5 shows the addition of a conventional vanadium catalyst to the boron phosphate.

TABLE

| Example No. | 1 | 2 | 3 | 4 | 5 | 6 | 7 | 8* | 9* | 10 |
|---|---|---|---|---|---|---|---|---|---|---|
| Reactants | | | | | | | | | | |
| 2-Methylbutene-2, g. | 500 | 500 | 500 | 500 | 500 | 500 | 500 | 500 | 500 | 500 |
| Boron Phosphate, g. | 1.0 | 1.0 | 1.0 | 2.0 | 1.0 | 1.0 | — | — | — | — |
| Phosphoric Acid, g | — | — | — | — | — | — | 0.5 | — | — | — |
| Vanadyl Acetylacetonate, g. | — | — | — | — | 0.2 | — | — | — | — | — |
| Lithium Phosphate g. | — | — | — | — | — | — | — | — | — | 1.0 |
| Reaction Conditions | | | | | | | | | | |
| Temperature, ° C | 90 | 90 | 100 | 100 | 90 | 90 | 90 | 90 | 90 | 90 |

TABLE-continued

| Example No. | 1 | 2 | 3 | 4 | 5 | 6 | 7 | 8* | 9* | 10 |
|---|---|---|---|---|---|---|---|---|---|---|
| Total Reaction Time, Hrs. | 4.25 | 3.33 | 3.42 | 1.48 | 4.17 | 5.63 | 4.50 | 3.50 | 2.03 | 7.67 |
| Results | | | | | | | | | | |
| Induction Period, min. | 154 | 62 | 172 | 30 | 77 | 106 | 118 | 138 | 73.5 | 156 |
| Oxygen Consumed, mole | 0.692 | 1.308 | 0.815 | 0.851 | 1.221 | 1.581 | 0.706 | 2.302 | 0.917 | 0.945 |
| Carbon Dioxide Produced, mole | 0.003 | 0.001 | 0.002 | 0.002 | 0.001 | 0.003 | 0.010 | 0.051 | 0.009 | 0.003 |
| 2-Methylbutene-2 conversion mole % | 8.8 | 13.8 | 7.7 | 9.6 | 11.5 | 22.2 | 6.9 | 33.9 | 9.4 | 7.3 |
| % Selectivity (Mole Product/100 Mole Olefin Consumed) | | | | | | | | | | |
| Acetaldehyde | 10.7 | 3.5 | 5.6 | 11.8 | 9.6 | 8.9 | 12.4 | 24.2 | 29.5 | 7.3 |
| Acetone | 15.4 | 12.8 | 14.1 | 23.4 | 18.9 | 22.9 | 23.8 | 41.6 | 36.9 | 13.7 |
| Methyl Isopropyl Ketone | 3.7 | 4.3 | 3.8 | 2.5 | 5.5 | 1.3 | 8.1 | 1.6 | 1.5 | 9.6 |
| 2,3-Epoxy-2-Methylbutane | 52.9 | 65.8 | 59.8 | 48.3 | 65.3 | 49.2 | 25.7 | 13.8 | 10.9 | 61.9 |
| 2-Methylbutane-2,3-diol | 5.7 | 2.1 | 5.2 | 5.6 | 2.3 | (a) | (a) | (a) | (a) | (a) |
| Olefin Hydroperoxide | 14.8 | 12.7 | 14.6 | 14.9 | 5.1 | 20.2 | 27.5 | 30.2 | 38.5 | 8.5 |

*600 psi oxygen pressure
(a) Trace

The invention claimed is:

1. A process for the autoxidation of ethylenically unsaturated hydrocarbon compounds containing from 2 to 30 carbon atoms to produce oxirane compounds, said process comprising contacting said hydrocarbon compounds with molecular oxygen in the presence of boron phosphate at a temperature of from about 70° C to about 120° C and a pressure sufficient to maintain said hydrocarbon compounds in liquid phase, said boron phosphate being present in an amount of from about 0.05 to about 0.8 weight percent based on said hydrocarbon compounds.

2. The process according to claim 1 wherein the temperature is from about 80° C to about 110° C.

3. The process according to claim 1 wherein the boron phosphate is present in an amount of 0.1 to 0.4 weight percent.

4. The process according to claim 1 wherein the ethylenically unsaturated organic hydrocarbon is selected from the group consisting of ethylene, propylene, butene-1, butene-2, isobutene, pentene-1, pentene-2, hexene, isohexene, heptene, 3-methyl-hexene-1, octene-1, isooctene, nonene, decene, dodecene, tridecene, pentadecene, octadecene, eicosene, docosene, tricosene, tetracosene, pentacosene, styrene, methyl styrene, vinyl toluene, pentadiene, hexadiene, octadiene, decadiene, tridecadiene, eicosadiene, tetracosadiene, cyclopentene, cyclohexene, cycloheptene, methyl cyclohexene, isopropylcyclohexene, butylcyclohexene, octaylcyclohexene, dodecylcyclohexene, vinyl cyclohexene and phenyl cyclohexene.

5. The process according to claim 4 wherein the ethylenically unsaturated hydrocarbon has 3 to 12 carbon atoms.

6. The process according to claim 3 wherein the ethylenically unsaturated hydrocarbon has 5 carbon atoms.

7. In the process of producing oxirane compounds by autoxidation of ethylenically unsaturated hydrocarbon compounds containing from 3 to 12 carbon atoms comprising contacting said hydrocarbon compound in liquid phase with molecular oxygen in the presence of a catalyst at 70° to 120° C at a sufficient pressure to maintain said liquid phase wherein the improvement comprises using boron phosphate in a quantity of from about 0.05 to about 0.8 weight percent based on the weight of said hydrocarbon compound as said catalyst.

* * * * *